(12) United States Patent
Cheng et al.

(10) Patent No.: US 10,663,336 B2
(45) Date of Patent: May 26, 2020

(54) PROCESSING CHAMBER GAS DETECTION SYSTEM AND OPERATION METHOD THEREOF

(71) Applicant: Winbond Electronics Corp., Taichung (TW)

(72) Inventors: Chi-We Cheng, Taichung (TW); Pei-Yu Chen, Taichung (TW)

(73) Assignee: WINBOND ELECTRONICS CORP., Taichung (TW)

(*) Notice: Subject to any disclaimer, the term of this patent is extended or adjusted under 35 U.S.C. 154(b) by 288 days.

(21) Appl. No.: 15/861,149

(22) Filed: Jan. 3, 2018

(65) Prior Publication Data

US 2018/0364084 A1 Dec. 20, 2018

(30) Foreign Application Priority Data

Jun. 20, 2017 (CN) .......................... 2017 1 0468217

(51) Int. Cl.

| | | |
|---|---|---|
| *G01F 3/22* | (2006.01) | |
| *G01M 3/32* | (2006.01) | |
| *G01L 19/12* | (2006.01) | |
| *C23C 16/44* | (2006.01) | |
| *G05D 11/13* | (2006.01) | |

(Continued)

(52) U.S. Cl.
CPC ............. *G01F 3/22* (2013.01); *C23C 16/4412* (2013.01); *G01L 19/12* (2013.01); *G01M 3/32* (2013.01); *G01N 33/0027* (2013.01); *G05D 11/132* (2013.01); *H01L 21/67017* (2013.01); *H01L 21/67109* (2013.01); *H01L 21/67253* (2013.01)

(58) Field of Classification Search
CPC ...... G01F 3/22; G01M 3/32; H01L 21/67017; H01L 21/67253; H01L 21/67109; G01N 33/0027; G05D 11/132; G01L 19/12; C23C 16/4412
USPC .......... 55/437, 385.1; 95/272; 118/733, 704, 118/715, 724; 257/E21.459
See application file for complete search history.

(56) References Cited

U.S. PATENT DOCUMENTS

| | | | | |
|---|---|---|---|---|
| 5,277,215 A | * | 1/1994 | Yanagawa | ......... C23C 16/45561 137/14 |
| 2009/0064765 A1 | * | 3/2009 | Megawa | ................. G01M 3/26 73/40.7 |

(Continued)

FOREIGN PATENT DOCUMENTS

| | | |
|---|---|---|
| CN | 201689872 U | 12/2010 |
| CN | 102373445 B | 1/2014 |

(Continued)

*Primary Examiner* — Minh Chau T Pham
(74) *Attorney, Agent, or Firm* — Muncy, Geissler, Olds & Lowe, P.C.

(57) ABSTRACT

A processing chamber gas detection system is provided, including a chamber, an exhaust pipe, a connection pipe, and a gas detector. The chamber is configured to perform a chemical vapor deposition (CVD) process. The exhaust pipe is connected to the chamber and the pumping unit, and the connecting pipe communicates with the exhaust pipe. The gas detector is disposed on the connecting pipe and configured to detect the oxygen content in the air from the chamber. When the air in the chamber is pumped out via the pumping unit and the air flows through the exhaust pipe and the connecting pipe, the gas detector detects whether oxygen is contained in the air or not.

20 Claims, 4 Drawing Sheets

(51) Int. Cl.
*H01L 21/67* (2006.01)
*G01N 33/00* (2006.01)

(56) References Cited

U.S. PATENT DOCUMENTS

| | | | |
|---|---|---|---|
| 2012/0180663 A1* | 7/2012 | Easton | B01D 45/08 95/272 |
| 2014/0357058 A1* | 12/2014 | Takagi | H01L 21/0262 438/478 |
| 2015/0107771 A1* | 4/2015 | Kobayashi | H01J 37/32834 156/345.29 |
| 2017/0088948 A1* | 3/2017 | Takagi | C23C 16/4401 |
| 2018/0204742 A1* | 7/2018 | Tateno | H01L 21/67017 |
| 2018/0274093 A1* | 9/2018 | Takagi | C23C 16/4402 |
| 2019/0186000 A1* | 6/2019 | Inada | H01L 21/67288 |

FOREIGN PATENT DOCUMENTS

| | | |
|---|---|---|
| TW | 200633792 A | 10/2006 |
| TW | M490506 U | 11/2014 |

* cited by examiner

PROCESSING CHAMBER GAS DETECTION SYSTEM AND OPERATION METHOD THEREOF

CROSS REFERENCE TO RELATED APPLICATIONS

This application claims the benefit of China Patent Application No. 201710468217.9, filed on Jun. 20, 2017, the entirety of which is incorporated by reference herein.

BACKGROUND OF THE INVENTION

Field of the Invention

The application relates in general to a processing chamber gas detection system and an operation method thereof, and in particular to a detection system that includes a gas detector and operation method thereof.

Description of the Related Art

In the semiconductor industry, a chemical vapor deposition (CVD) process is often used to form films. In a general CVD process, a wafer (or substrate) is exposed to one or more different precursors, and the chemical reaction and/or chemical decomposition occurs on the surface of the substrate to deposit the desired films. During the reaction, one or more different by-products are usually produced. By exhausting/pumping the reaction chamber, those by-products can be removed. The current CVD process usually uses low-pressure chemical vapor deposition (LPCVD) in a low-pressure environment, to reduce unnecessary gaseous reaction (due to the lower pressure of the environment), to increase the uniformity of the films on the wafer.

With the evolution of semiconductor technology, the requirements for quality of the product in the process have relatively improved, so the accuracy of the pressure control in the chamber and the degree of fitting between the chamber and the pipeline are relatively strict. However, due to the long-term use of such elements, the chamber, the pipeline, or the junction therebetween may deteriorate, and then one or more cracks may occur, and these cracks may lead to a decline in the precision and quality of the overall process. Therefore, in order to improve the quality of the process, it has become an increasingly important issue to provide an accurate and immediate detection mechanism to each element and to determine whether or not the elements have cracks or leaks.

A common leak detection system used to detect a reaction chamber for LPCVD, often provides a pressure detector to detect the air pressure in the chamber. When pumping the air out of the chamber and maintaining the air pressure for a period of time, if the pressure changes in the predetermined time, the leakage rate can be calculated by the pressure change over time (pressure divided by time), which indicates that there is an atmospheric invasion. However, the pressure detector provided in the detection system may experience measurement error (detection error) of the gas pressure in the chamber, so that when a tiny leak detection (e.g., the air pressure in the chamber is less than $10^{-4}$ mbar) is to be performed, it cannot reflect the real situation of the leakage in the chamber due to the measurement error.

BRIEF SUMMARY OF INVENTION

To address the deficiencies of conventional processing chamber gas detection systems, an embodiment of the invention provides a processing chamber gas detection system, including a chamber, an exhaust pipe, a connection pipe, and a gas detector. The chamber is configured to perform a chemical vapor deposition (CVD) process. The exhaust pipe is connected to the chamber and the pumping unit, and the connecting pipe communicates with the exhaust pipe. The gas detector is disposed on the connecting pipe and configured to detect the oxygen content in the air from the chamber. When the air in the chamber is pumped out via the pumping unit and the air pressure of the chamber is less than $10^{-8}$, the air flows from the exhaust pipe to the connecting pipe and the gas detector detects whether oxygen is contained in the air or not.

The invention also provides a method for operating a processing chamber gas detection system, including providing an exhaust pipe to connect a chamber and a pumping unit, wherein the chamber is configured to perform a chemical vapor deposition process; providing a connecting pipe to communicate with the exhaust pipe; disposed a first valve on the exhaust pipe; disposed a second valve and a gas detector on the connecting pipe; opening the first valve and pumping the air out of the chamber using the pumping unit to perform a first exhausting; opening the second valve, wherein the air from the chamber flows from the exhaust pipe to the connecting pipe; and detecting the oxygen content in the air from the chamber using the gas detector.

BRIEF DESCRIPTION OF DRAWINGS

The invention can be more fully understood by reading the subsequent detailed description and examples with references made to the accompanying drawings, wherein.

DETAILED DESCRIPTION OF INVENTION

The making and using of the embodiments of the processing chamber gas detection systems are discussed in detail below. It should be appreciated, however, that the embodiments provide many applicable inventive concepts that can be embodied in a wide variety of specific contexts. The specific embodiments discussed are merely illustrative of specific ways to make and use the embodiments, and do not limit the scope of the disclosure.

Unless defined otherwise, all technical and scientific terms used herein have the same meaning as commonly understood by one of ordinary skill in the art to which this invention belongs. It should be appreciated that each term, which is defined in a commonly used dictionary, should be interpreted as having a meaning conforming to the relative skills and the background or the context of the present disclosure, and should not be interpreted by an idealized or overly formal manner unless defined otherwise.

Figure 1:
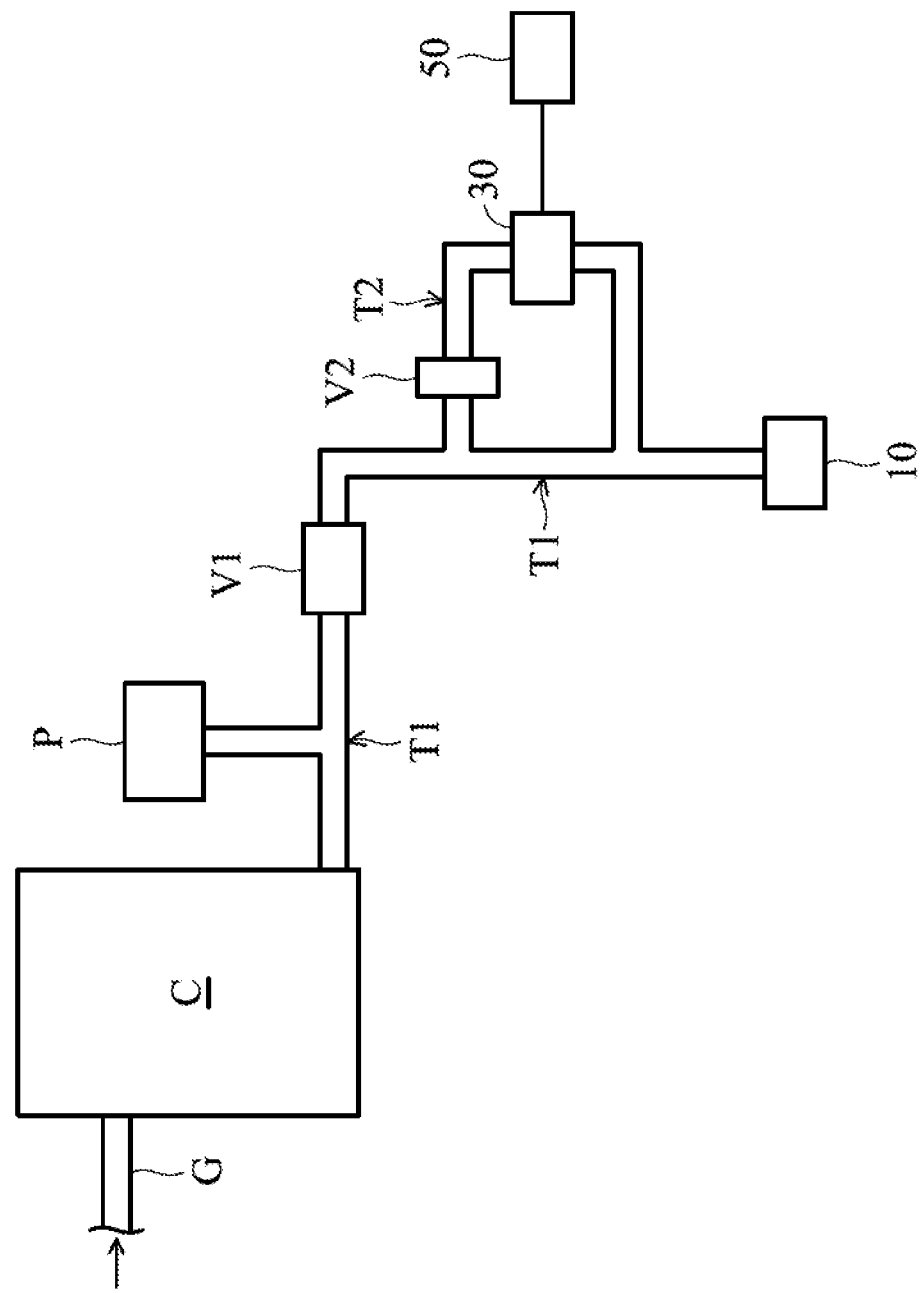
FIG. 1 is a schematic diagram of a processing chamber gas detection system according to an embodiment of the invention.

FIG. 1 is a schematic diagram of a processing chamber gas detection system according to an embodiment of the invention. As shown in FIG. 1, the processing chamber gas detection system may arranged in a semiconductor factory and includes a chamber C, wherein the chamber C, for example, is a reactor for growing films by chemical vapor deposition (CVD) in a semiconductor process, so that one or more wafers are exposed to one or more different precursors and a chemical reaction and/or chemical decomposition occurs on their surfaces to deposit the films. The chamber C may be used as a reactor configured to perform low-pressure chemical vapor deposition (LPCVD), and the reaction temperature of which is carried out at a high temperature (e.g., 600 to 1000° C.). When the film is deposited, the air pressure in the chamber C is lowered to, for example, about 100 mbar or less, so that the reaction is carried out at a low pressure such that the deposited film has a better step coverage capability and thickness uniformity. The general deposition materials used in CVD are, for example, silicon dioxide, silicon nitride, polysilicon, or metalloid silicides.

Please continue refer to FIG. 1, the processing chamber gas detection system further comprises a pumping unit 10, a gas detector 30, an exhaust pipe T1, a connecting pipe T2, a first valve V1, a second valve V2, and a controller 50. The exhaust pipe T1 communicates with the chamber C and the pumping unit 10, so that the pumping unit 10 can exhaust the air in the chamber C via the exhaust pipe T1. The connecting pipe T2 with a U-shaped structure is connected to the exhaust pipe T1 (two ends of the U-shaped structure are communicated with the exhaust pipe T1), so that the air in the chamber C may flow through the exhaust pipe T1 to the connecting pipe T2. The first and second valves V1 and V2 can control the flow rate of the air from the chamber C. When the first valve V1 is opened, the pumping unit 10 can be started to evacuate the chamber C. When the first and second valves V1 and V2 are opened, the air is allowed to flow from the exhaust pipe T1 through the connecting pipe T2, and the air is pumped out (exhausted out) via the pumping unit 10. In addition, the processing chamber gas detection system further comprises a pressure detector P disposed on the exhaust pipe T1, which is also connected to the exhaust pipe T1 and situated between the chamber C and the first valve V1, for detecting the air pressure in the chamber C.

In the present embodiment, the low-pressure chemical deposition reaction in the chamber C is accompanied by by-products, such as hydrogen, water, silicon tetrachloride, or hydrogen chloride (HCl), and the by-products can be withdrawn from the chamber C by the pumping unit 10, so that the by-products can be discharged (e.g., discharged to an exhaust gas washing system), to achieve the purpose of prevention and control of semiconductor pollutants.

As shown in FIG. 1, the gas detector 30 is disposed on one end of the connecting pipe T2, such as an oxygen detector which is configured to detect the oxygen content of the air in the chamber C, to detect whether the air or other gas from the atmosphere entering the chamber C due to the chamber C having cracks or the junction between the chamber C and the pipe being loose. More specifically, in the present embodiment, when the continuous silicon film is grown on the substrate in the chamber C in the CVD process, the chemicals used therein do not contain oxygen, and if there is excess oxygen presenting in the chamber C, it may cause the substrate to be cluttered with silicon oxide film. Therefore, it is possible to use a gas detector 30 to detect whether or not the air in the chamber C contains oxygen, and to help to determine whether or not the chamber C, the exhaust pipe T1, or the connecting pipe T2 is cracked and leaking, or air from the atmosphere is entering.

In particular, the gas detector 30 converts the substance to be measured (oxygen) in the air into an appropriate electrical signal (e.g., voltage, current, or resistance) for measurement. For example, a predetermined value is provided in the gas detector 30 beforehand, and then the gas detector 30 detects the specific gas content to obtain a measured value and compare it with the aforementioned predetermined value, to determine whether or not that specific gas exists. After that, the gas detector 30 may deliver the information to the controller 50, so that the controller 50 can inform a process operator to know the current situation detected by gas detector 30.

The real-time detection for the chamber C is described in detail below. First, the reaction gas is fed to the chamber C via an inlet pipe G, to react with one or more substrates (or wafers) in the chamber C to perform a CVD process. Then, the chamber C is evacuated by the pumping unit 10 by opening the first valve V1, to remove by-products generated during the process, and when the air pressure in the chamber C is pumped to a low-pressure environment (for example, less than $10^{-8}$ mbar), the second valve V2 is opened so that the air flows from the exhaust pipe T1 to the connecting pipe T2. The gas detector 30 detects the air flowing out of the chamber C to detect whether the air contains oxygen or not. If the detected current electrical signal is higher than the predetermined electrical signal to a predetermined degree, it is determined that an outer gas or air intrudes the chamber C and/or the pipes. In other words, in the low-pressure environment, the gas detector 30 can detect whether or not there is any slight or tinny leak in the real time of the chamber C executing the CVD process, so that an appropriate cure can be made in time. Thus, the CVD process in the chamber C can be maintained in a high quality level.

It should be noted that there is a distance between the gas detector 30 and the chamber C. In the present embodiment, the distance is at least 25 meters (or more than 25 meters). Since the chamber C is, a high temperature reaction furnace for performing a CVD process, with a high working temperature of about 600 to 1000° C., if the gas detector 30 is disposed too close to the chamber C, the gas detector 30 may be destroyed or failed due to the high temperature. It is possible to stably and safely achieve immediate monitoring of the chamber C in the CVD process by providing the gas detector 30 at least 25 meters above the chamber C.

Figure 2:
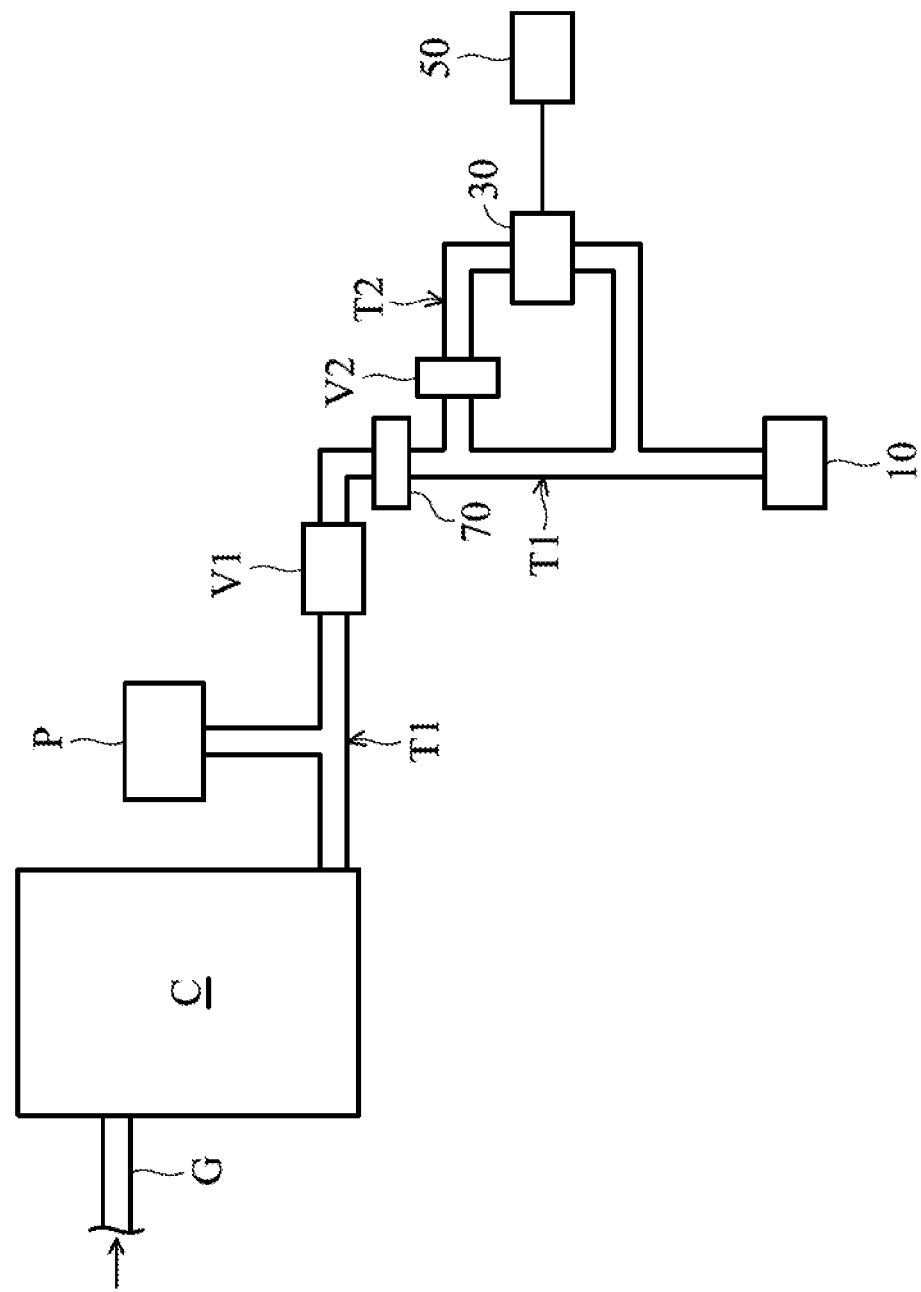
FIG. 2 is a schematic diagram of a processing chamber gas detection system according to another embodiment of the invention.

FIG. 2 is a schematic diagram of a processing chamber gas detection system according to another embodiment of the invention. The main difference between the present and the aforementioned (FIG. 1) embodiments is that the processing chamber gas detection system in present embodiment further comprises a trap 70 disposed on the exhaust pipe T1, configured to adsorb, filter, and trap particles or dust in the air exhausted by the pumping unit 10. It is to be noted that the trap 70 is disposed on the upstream of the exhaust pipe T1 and closer to the chamber C than the gas detector 30. Therefore, the air from the chamber C can be trapped by the trap 70 before flowing to the gas detector 30 so that the gas detector 30 can perform the oxygen detection more efficiently, and the occurrence of clogging of the exhaust pipe T1 can be avoided or reduced.

Figure 3:
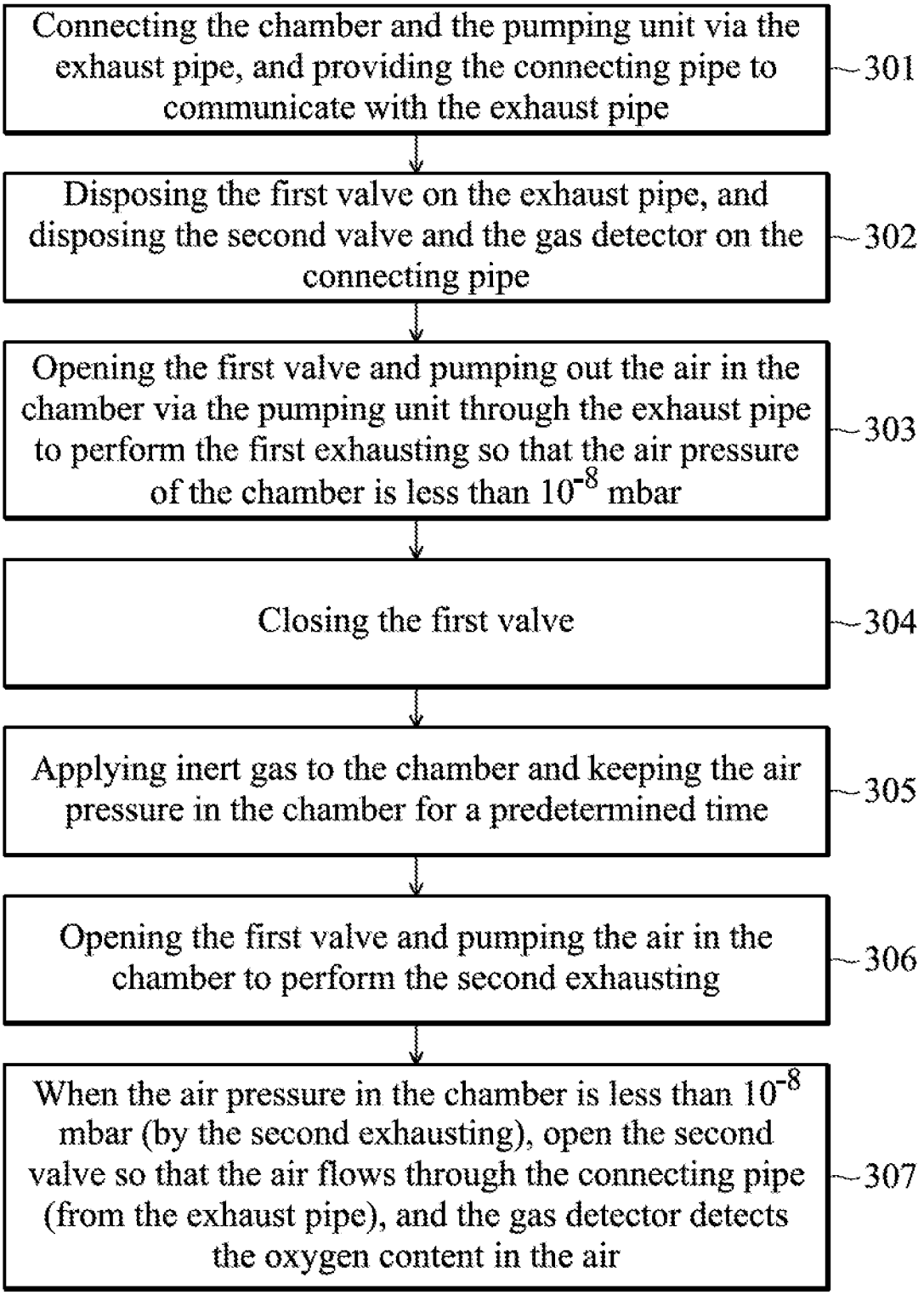
FIG. 3 is a flow chart diagram of method of operating the processing chamber gas detection system according to an embodiment of the invention.

According to the foregoing description, the present invention also provides a method of operating a process chamber gas detection system. As shown in FIG. 3, first, provide an exhaust pipe T1 to connect a chamber C and a pumping unit 10, and provide a connecting pipe T2 communicated with the exhaust pipe T1 (step 301), wherein the chamber C is a chamber for performing a CVD process. Next, dispose a first valve V1 on the exhaust pipe T1, and dispose a second valve V2 and a gas detector 30 on the connecting pipe T2 (step 302), wherein the gas detector 30 is disposed at least 25 meters away from the chamber C. After then, open the first valve V1, and pumping (exhausting) the air out of the chamber C using the pumping unit 10 through the exhaust pipe T1 to perform a first exhausting, and the air pressure in the chamber C is less than $10^{-8}$ mbar by performing the first exhausting (after the first exhausting is performed) (step 303). Then, close the first valve V1 (step 304), and apply an inert gas into the chamber C (for example, apply helium via the inlet pipe G) and maintain the air pressure in the chamber C for a predetermined time (e.g. 5 to 10 minutes) (step 305). Open the first valve V1 and pump the air out of the chamber C with the pumping unit 10 to perform a second exhausting (step 306). After that, when the air pressure in the chamber C is less than $10^{-8}$ mbar (by the second exhausting), open the second valve V2 so that the air in the chamber flows from the exhaust pipe T1 to the connecting pipe T2, and the gas detector 30 detects the oxygen content in the air (step 307). In this way, the detection of the oxygen content in the air via the gas detector 30 can determine whether the chamber or the pipe has any slight breakage or leakage, so that the CVD process can be stopped in time and properly treated, to avoid producing excessive defective products.

By step 304 (applying an inert gas to the chamber C), the air in the chamber C can flow effectively so that the second exhausting (step 306) can be performed more efficiently. On the other hand, maintaining the air pressure in the chamber C for a predetermined time (step 305) allows the inert gas to be evenly distributed in the chamber C for a sufficient amount of time, so that the second exhausting (step 306) can be carried out more efficiently, and the measurement for the oxygen content (via the gas detector 30) in the air can be more accurate. Furthermore, a trap 70 may be provided on the exhaust pipe T1, wherein the position of the trap 70 is closer to the chamber C than the gas detector 30. When the air in the chamber C pumped out via the exhaust unit 10, the particles in the air are filtered through the trap 70.

In another embodiment, however, step 305 (maintaining the air pressure in the chamber C in for a predetermined time) may be omitted, and the first and second valves V1 and V2 may be directly opened after applying the inert gas in the chamber C, so that the air flows from the exhaust pipe T1 to the connecting pipe T2 and the gas detector 30 detects the oxygen content in the air.

Figure 4:
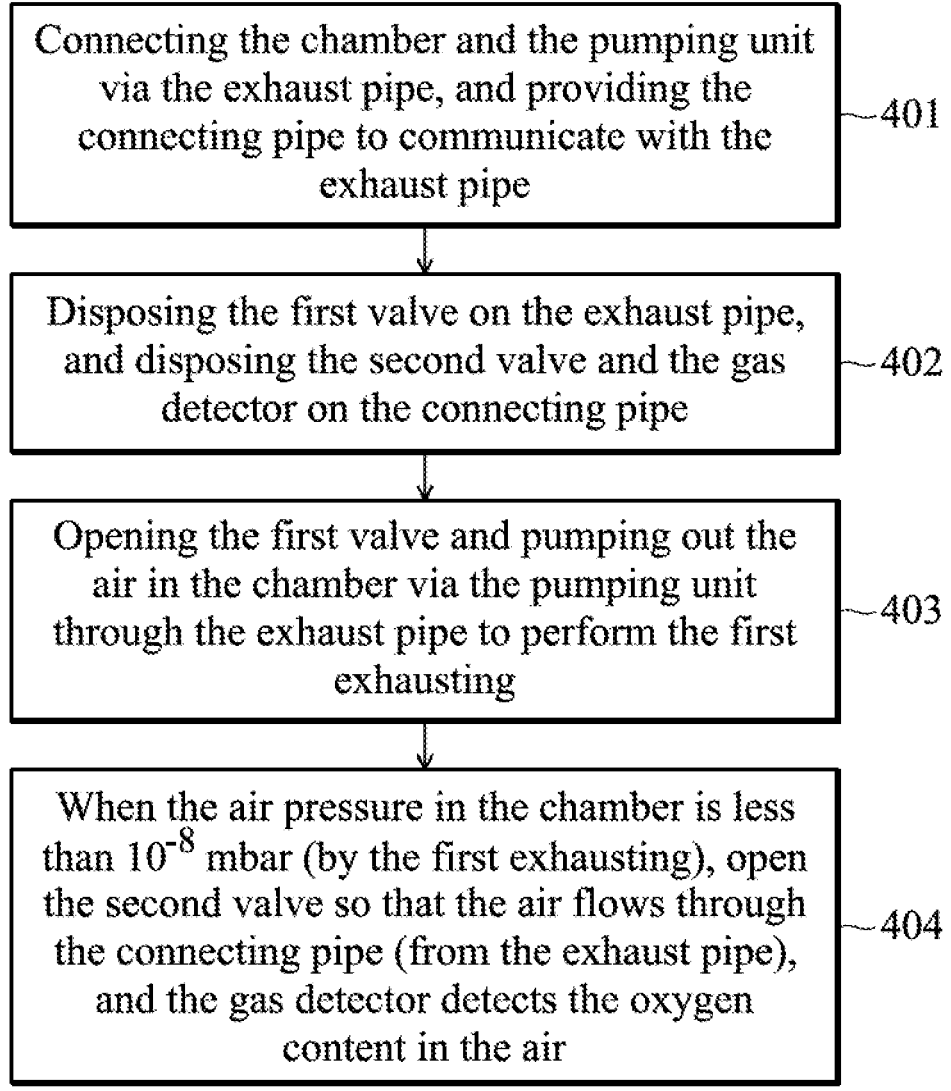
FIG. 4 is a flow chart diagram of method of operating the processing chamber gas detection system according to another embodiment of the invention.

Moreover, the present invention further provides another method of operating a process chamber gas detection system. As shown in FIG. 4, it is different from the aforementioned operation method (FIG. 3) mainly in that, when the chamber C is subjected to a first exhausting (step 403) and the air pressure in the chamber C is less than (or equal to) $10^{-8}$ mbar, the second valve V2 is directly opened to allow the air from the chamber C to flow through the connecting pipe T2 (from the exhaust pipe T1), so that the gas detector 30 can detect the oxygen content in the air (step 404).

In summary, a processing chamber gas detection system is provided, including a chamber, an exhaust pipe, a connection pipe, and a gas detector. The chamber is configured to perform a chemical vapor deposition (CVD) process. The exhaust pipe is connected to the chamber and the pumping unit, and the connecting pipe communicates with the exhaust pipe. The gas detector is disposed on the connecting pipe and configured to detect the oxygen content in the air from the chamber. When the air in the chamber is pumped out via the pumping unit and the air pressure of the chamber is less than $10^{-8}$, the air flows from the exhaust pipe to the connecting pipe and the gas detector detects whether oxygen is contained in the air or not. Therefore, by using the gas detector to check whether the chamber has any tiny leaks or cracks, the CVD process can be stopped quickly and an appropriate treatment can be made, to avoid excessive production of bad products, thereby enhancing the quality of the process.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term) to distinguish the claim elements.

It will be apparent to those skilled in the art that various modifications and variations can be made in the invention. It is intended that the standard and examples be considered as exemplary only, with a true scope of the disclosed embodiments being indicated by the following claims and their equivalents.

What is claimed is:

1. A processing chamber gas detection system, comprising:
   a chamber, configured to perform a chemical vapor deposition process;
   a pumping unit;
   an exhaust pipe, connecting the chamber and the pumping unit;
   a connecting pipe, communicating with the exhaust pipe;
   a first valve, disposed on the exhaust pipe;
   a second valve, disposed on the connecting pipe; and
   a gas detector, disposed on the connecting pipe;
   wherein the pumping unit pumps air out of the chamber through the first valve and the exhaust pipe,
   wherein when the air in the chamber is pumped out by the pumping unit, the air pumped out of the chamber flows through the connecting pipe via the second valve and the gas detector detects an oxygen content in the air.

2. The processing chamber gas detection system as claimed in claim 1, wherein when an air pressure of the chamber is less than $10^{-8}$ mbar, the gas detector detects the oxygen content in the air flowing through the connecting pipe.

3. The processing chamber gas detection system as claimed in claim 1, wherein there is a distance between the chamber and the gas detector, and the distance is at least 25 meters.

4. The processing chamber gas detection system as claimed in claim 1, wherein a temperature inside the chamber is greater than 600° C. when the gas detector detects the oxygen content in the air from the chamber.

5. The processing chamber gas detection system as claimed in claim 1, wherein the connecting pipe has a U-shaped structure, and two ends of the U-shaped structure communicate with the exhaust pipe.

6. The processing chamber gas detection system as claimed in claim 1, further comprising a trap disposed on the connecting pipe, wherein when the air from the chamber is exhausted by the pumping unit through the exhaust pipe and the connecting pipe, the trap filters particles in the air.

7. The processing chamber gas detection system as claimed in claim 6, wherein the trap is closer to the chamber than the gas detector.

8. The processing chamber gas detection system as claimed in claim 1, further comprising a pressure detector disposed on the exhaust pipe, configured to detect the air pressure in the chamber.

9. The processing chamber gas detection system as claimed in claim 8, wherein the pressure detector is disposed between the chamber and the first valve.

10. A method for operating a processing chamber gas detection system, comprising:
providing an exhaust pipe to connect a chamber and a pumping unit, wherein the chamber is configured to perform a chemical vapor deposition process;
providing a connecting pipe to communicate with the exhaust pipe;
disposing a first valve on the exhaust pipe;
disposing a second valve and a gas detector on the connecting pipe;
opening the first valve and pumping the air out of the chamber using the pumping unit to perform a first exhausting;
opening the second valve, wherein the air from the chamber flows from the exhaust pipe to the connecting pipe; and
detecting an oxygen content in the air by using a gas detector after the air is pumped out of the chamber and flows through the connecting pipe.

11. The method for operating a processing chamber gas detection system as claimed in claim 10, wherein the air pressure in the chamber is less than 10-8 mbar after the first exhausting is performed.

12. The method for operating a processing chamber gas detection system as claimed in claim 10, further comprising:
applying an inert gas into the chamber and pumping the air out of the chamber using the pumping unit to perform a second exhausting after the step of performing the first exhausting and before the step of opening the second valve.

13. The method for operating a processing chamber gas detection system as claimed in claim 10, further comprising:
after the step of performing the first exhausting and before the step of opening the second valve, closing the first valve and applying an inert gas to the chamber, to maintain the pressure in the chamber for 5-10 minutes, and then opening the first valve and pumping the air out of the chamber using the pumping unit to perform a second exhausting.

14. The method for operating a processing chamber gas detection system as claimed in claim 10, wherein there is a distance between the chamber and the gas detector, and the distance is at least 25 meters.

15. The method for operating a processing chamber gas detection system as claimed in claim 10, wherein the temperature inside the chamber is greater than 600° C. when the gas detector detects the oxygen content in the air from the chamber.

16. The method for operating a processing chamber gas detection system as claimed in claim 10, wherein the connecting pipe has a U-shaped structure, and two ends of the U-shaped structure communicate with the exhaust pipe.

17. The method for operating a processing chamber gas detection system as claimed in claim 10, further comprising:
disposing a trap on the exhaust pipe, wherein when the pumping unit performs the first pumping of the air from the chamber, the trap filters particles in the air.

18. The method for operating a processing chamber gas detection system as claimed in claim 17, wherein the trap is closer to the chamber than the gas detector.

19. The method for operating a processing chamber gas detection system as claimed in claim 10, further comprising:
disposing a pressure detector on the exhaust pipe, configured to detect the air pressure in the chamber.

20. The method for operating a processing chamber gas detection system as claimed in claim 19, wherein the pressure detector is disposed between the chamber and the first valve.

* * * * *